US009603827B2

(12) United States Patent
Okada et al.

(10) Patent No.: US 9,603,827 B2
(45) Date of Patent: Mar. 28, 2017

(54) METHOD FOR PREVENTING AND/OR TREATING HAIRY WART DISEASE

(71) Applicants: Mitsubishi-Kagaku Foods Corporation, Chiyoda-ku (JP); Incorporated National University Iwate University, Morioka-shi (JP)

(72) Inventors: Keiji Okada, Morioka (JP); Yasushi Sekiyama, Chiyoda (JP)

(73) Assignees: MITSUBISHI-KAGAKU FOODS CORPORATION, Chiyoda-ku (JP); INCORPORATED NATIONAL UNIVERSITY IWATE UNIVERSITY, Morioka-shi (JP)

(*) Notice: Subject to any disclaimer, the term of this patent is extended or adjusted under 35 U.S.C. 154(b) by 0 days.

(21) Appl. No.: 14/984,655

(22) Filed: Dec. 30, 2015

(65) Prior Publication Data

US 2016/0106701 A1 Apr. 21, 2016

Related U.S. Application Data

(63) Continuation of application No. PCT/JP2014/067769, filed on Jul. 3, 2014.

(51) Int. Cl.
*A61K 31/21* (2006.01)
*A61K 31/26* (2006.01)
*A61K 9/00* (2006.01)

(52) U.S. Cl.
CPC ............ *A61K 31/26* (2013.01); *A61K 9/0017* (2013.01)

(58) Field of Classification Search
USPC ........................................................ 514/514
See application file for complete search history.

(56) References Cited

U.S. PATENT DOCUMENTS

| | | | | |
|---|---|---|---|---|
| 5,703,124 A | * | 12/1997 | Takata | A01N 3/00 514/514 |
| 6,028,104 A | | 2/2000 | Schmidt et al. | |
| 7,799,782 B2 | * | 9/2010 | Munson | C07D 231/56 514/234.5 |
| 2009/0110645 A1 | | 4/2009 | Morelli et al. | |
| 2010/0137451 A1 | | 6/2010 | Demarco et al. | |
| 2013/0034560 A1 | | 2/2013 | Rosander et al. | |
| 2013/0172425 A1 | | 7/2013 | Demarco et al. | |

FOREIGN PATENT DOCUMENTS

| | | |
|---|---|---|
| JP | 2002-501480 | 1/2002 |
| JP | 4198193 | 12/2008 |
| JP | 2011-500790 | 1/2011 |
| JP | 2012-510469 | 5/2012 |
| JP | 2013-518563 | 5/2013 |
| RU | 2 248 209 | 3/2005 |
| WO | WO 98/33490 | 8/1998 |
| WO | WO2008/082692 * | 7/2008 |
| WO | WO 2009/053934 A2 | 4/2009 |
| WO | WO 2010/062961 A1 | 6/2010 |
| WO | WO 2011/093783 A1 | 8/2011 |

OTHER PUBLICATIONS

Rusakova et al. CAS: 142: 303661, 2005.*
International Search Report issued Jul. 29, 2014 in PCT/JP2014/067769, filed Jul. 3, 2014 (with English Translation).
Written Opinion issued Jul. 29, 2014 in PCT/JP2014/067769, filed Jul. 3, 2014.
Yasushi Sekiyama "Antimicrobial Effect and its Application of Mustard Extract and Hop Extract", Food Chemicals, vol. 29, No. 2, Feb. 1, 2013, 12 pages. (with Computer Generated Partial English Translation).
Yasushi Sekiyama et al. "6. Control of Salmonella by Allylmustard Oil", The Japanese Society of Farm Animal Veterinary Medicine, The Japanese Society of Small Animal Veterinary Medicine, The Japanese Society of Veterinary Public Health Medicine Heisei 5 Nendo Gakkai Nenji Taikai Program, vol. 1993, Feb. 1994, 5 pages. (with Computer Generated English Translation).
Takumi Yamamoto et al. "18. Therapeutic Effect of Allyl Isothiocyanate Against Bovine Digital Dermatitis", Japanese Journal of Large Animal Clinics Heisei 25 Nendo Dai 44 Kai, Japanese Society of Veterinary Clinics Gakujutsu Shukai Ippan Koen Shoroku, vol. 4, No. 2, Nov. 2013, 6 pages. (with Computer Generated English Translation).
Kanako Chiba et al. "HL-7: The Relationship Between Gait and Disease State of a Cow Affected with Digital Dermatitis", Dai 156 Kai Japanese Society of Veterinary Science Gakujutsu Shukai Koen Yoshishu, vol. 156, Aug. 30, 2013, 5 pages. (with Computer Generated English Translation).
European Search Report issued Dec. 5, 2016 as received in the corresponding European Patent Application No. 14820387.0.

* cited by examiner

*Primary Examiner* — Rei-Tsang Shiao
(74) *Attorney, Agent, or Firm* — Oblon, McClelland, Maier & Neustadt, L.L.P.

(57) ABSTRACT

Provided is a novel method for preventing and/or treating hairy wart disease which is a hoof and leg disease of ungulates. The method is carried out by administering an isothiocyanic acid ester such as allyl isothiocyanate to a hoof of an ungulate. Examples of ungulates targeted for application of the present invention include cows such as dairy cows as well as sheep, pigs and horses.

11 Claims, 3 Drawing Sheets day0　　Sodium alginate　day2 day0　　Slaked lime　day2

Allyl isothiocyanate day0      Allyl isothiocyanate      day7

METHOD FOR PREVENTING AND/OR TREATING HAIRY WART DISEASE

TECHNICAL FIELD

The present invention relates to a method for preventing and/or treating hairy wart disease which is a hoof and leg disease of ungulates.

BACKGROUND ART

Hairy wart disease is an infectious disease that propagates among cows and other ungulates. Digital dermatitis (DD) is known to be a particularly serious hoof and leg disease caused by bacteria belonging to the genus *Treponema*, and in the case dairy cows have become afflicted with this disease, can lead to serious gait disorders or weight loss and the like as well as cause decreased milk production, thereby making it a serious problem in numerous dairy product-producing countries including Japan. As methods used to prevent and/or treat hairy wart disease in dairy cows, a foot bath wherein hoof baths containing medicinal agents, such as sodium alginate, copper sulfate, slaked lime or antibiotics (such as lincomycin) are placed in a barn and dairy cows are allowed to pass there through, is currently employed. However, effects in the case of using sodium alginate, copper sulfate or slaked lime are not satisfactory, and although effects are superior in the case of using antibiotics, there are problems such as the risk of the generation of drug-resistant microorganisms and the risk of milk being polluted through antibiotics. In addition, although, for example, a prevention and/or treatment method using peroxycarboxylic acid disclosed in Patent Document 1, a prevention and/or treatment method using a working liquid containing a metal astringent disclosed in Patent Document 2, and a prevention and/or treatment method using a composition containing a cross-linking agent disclosed in Patent Document 3 have been proposed, it is currently extremely important to develop a more effective prevention and/or treatment method.

PRIOR ART DOCUMENTS

Patent Documents

Patent Document 1: Japanese Patent No. 4198193
Patent Document 2: Japanese Unexamined Patent Application Publication (Translation of PCT Application) No. 2011-500790
Patent Document 3: Japanese Unexamined Patent Application Publication (Translation of PCT Application) No. 2012-510469

SUMMARY OF THE INVENTION

Problems to be Solved by the Invention

Therefore, an object of the present invention is to provide a novel method for preventing and/or treating hairy wart disease which is a hoof and leg disease of ungulates.

Means for Solving the Problems

As a result of conducting extensive studies with the foregoing in view, the inventors of the present invention found that an isothiocyanic acid ester, which is a pungent component of mustard or horseradish, has superior preventive and/or therapeutic effects against hairy wart disease.

As described in claim 1, the method for preventing and/or treating hairy wart disease of the present invention completed on the basis of the aforementioned finding is carried out by administering an isothiocyanic acid ester to the hoof of an ungulate.

In addition, as described in claim 6, a preventive and/or therapeutic agent for hairy wart disease of the present invention comprises an isothiocyanic acid ester as an active ingredient thereof.

Effects of the Invention

According to the present invention, a novel method for preventing and/or treatment hairy wart disease can be provided that uses an isothiocyanic acid ester.

In addition, the preventive and/or therapeutic agent for hairy wart disease of the present invention is able to effectively promote prevention and/or treatment because it has not a disagreeable odor to ungulates in comparison with other preventive and/or therapeutic agents.

MODE FOR CARRYING OUT THE INVENTION

Figure 1:
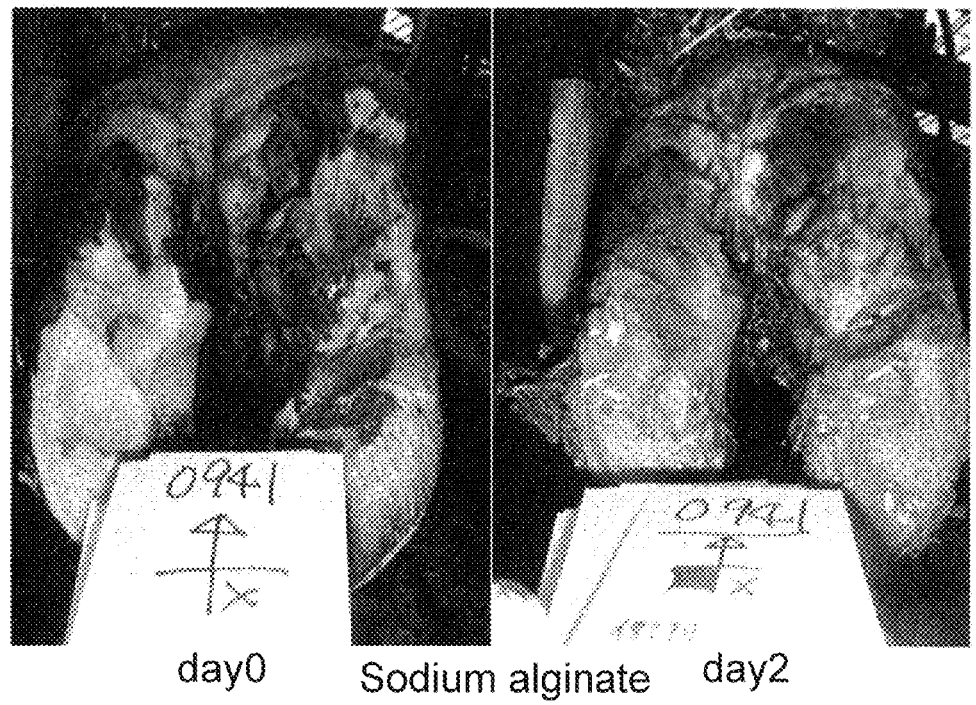
FIG. 1 is a photograph of an affected area at which the use of sodium alginate was effective in Example 1.

The method for preventing and/or treating hairy wart disease of the present invention is carried out by administering an isothiocyanic acid ester to a hoof of an ungulate. The onset of hairy wart disease can be prevented by prophylactically administering an isothiocyanic acid ester, and existing hairy wart disease can be cured by administering an isothiocyanic acid ester therapeutically.

In addition, although the preventive and/or therapeutic agent for hairy wart disease of the present invention contains an isothiocyanic acid ester as an active ingredient thereof, it can be used for prevention and treatment in the same manner as the aforementioned preventive and/or treatment method.

Examples of ungulates targeted for application of the present invention include cows such as dairy cows as well as sheep, pigs and horses. Hairy wart disease is a hoof and leg disease of such ungulates, and diseases such as the previously mentioned digital dermatitis as well as papillomatus digital dermatitis (PDD), infectious bovine interdigital dermatitis (IDD), stable foot rot (SFR) and hairy hoof wart attack (a hoof disease that causes ulceration following infiltration by a causative microorganism into the horny hoof through a gap in the hoof), which has become increasingly prevalent in recent years, are included in this category.

Specific examples of the isothiocyanic acid ester of the present invention include $C_{2-6}$ alkenyl isothiocyanates such as allyl isothiocyanate, aryl isothiocyanates such as phenyl isothiocyanate, $C_{1-6}$ alkyl isothiocyanates such as methyl isothiocyanate, ethyl isothiocyanate, propyl isothiocyanate, isopropyl isothiocyanate, butyl isothiocyanate, isobutyl isothiocyanate or isoamyl isothiocyanate, phenyl $C_{1-6}$ alkyl isothiocyanates such as benzyl isothiocyanate, and $C_{3-6}$ cycloalkyl isothiocyanates such as cyclohexyl isothiocyanate. $C_{2-6}$ alkenyl isothiocyanates, and allyl isothiocyanate in particular, are preferable from the viewpoint of demonstrating favorable preventive and/or therapeutic effects against hairy wart disease.

The isothiocyanic acid ester of the present invention may be a natural product extracted from mustard, horseradish or the like, or may be a synthetic product synthesized according to a known method. In addition, the isothiocyanic acid ester may be used alone or may be used by mixing a plurality of types thereof.

Although the method for preventing and/or treating hairy wart disease of the present invention is carried out by administering an isothiocyanic acid ester to a hoof of an ungulate, this isothiocyanic acid ester may be used as is in the form of isothiocyanic acid ester, or the preventive and/or therapeutic agent for hairy wart disease of the present invention may be used.

There are no special limitations on the method used to administer the isothiocyanic acid ester to a hoof of an ungulate, and in addition to a method consisting of the use of a foot bath that uses a hoof bath containing an isothiocyanic acid ester, a method consisting of applying an isothiocyanic acid ester by having animals step on a sheet impregnated therewith, a method consisting of spraying an aerosol propellant containing an isothiocyanic acid ester onto a hoof, a method consisting of applying an embrocation containing an isothiocyanic acid ester to a hoof, a method consisting of affixing a patch impregnated with an isothiocyanic acid ester to a hoof, or a method consisting of having animals step on a sheet impregnated with an isothiocyanic acid ester to transfer the isothiocyanic acid ester to a hoof thereof, can be employed. These methods may also be used in combination. Regardless of the method used, the onset of hairy wart disease can be prevented by carrying out these methods prophylactically, while existing hairy wart disease can be cured by carrying out therapeutically. Although isothiocyanic acid esters are highly volatile oily substances that may be administered directly, a water-soluble preparation, sprayable preparation or powdered composition thereof, obtained by dissolving or dispersing in a solvent or dispersion medium such as water, may also be used for the aforementioned administration as the preventive and/or therapeutic agent for hairy wart disease of the present invention, and a preferable preparation can be suitably selected and used corresponding to the administration method.

In the case of prevention in particular, a foot bath, a sheet, spray or embrocation containing an isothiocyanic acid ester, or a patch impregnated with an isothiocyanic acid ester, can be used preferably, the aforementioned spray or embrocation may be sprayed on or applied to a site having the possibility of being infected, or the aforementioned patch may be affixed thereto.

In addition, in the case of treatment, since the isothiocyanic acid ester is preferably administered to an affected area at a high concentration, although the aforementioned foot bath or sheet and the like may still be used, spraying or applying the aforementioned spray or embrocation, or affixing the aforementioned patch, directly to the affected area is preferable.

When administering an isothiocyanic acid ester to a hoof of an ungulate, the hoof is preferably cleaned by rinsing off any dirt or manure adhered to the hoof in advance with water and the like. For example, after first cleaning the hoof (affected area), the hoof may be first washed using water or by having the animal pass through a foot bath to remove any dirt and manure followed by spraying, applying or affixing the isothiocyanic acid ester. In addition, the isothiocyanic acid ester is also preferably administered after preliminarily trimming the hoof.

In addition, an automated administration system that uses an apparatus or sensor may also be used, and since this facilitates periodic administration of isothiocyanic acid, is effective for prevention in particular.

The dose of the isothiocyanic acid ester can be suitably set according to such factors as the type, age, body weight or degree of symptoms and the like of the ungulate targeted for prevention and/or treatment.

In addition, although there are cases in which a single administration of isothiocyanic acid ester may be sufficiently effective, it may also be administered periodically, and periodic administration is preferable particularly in the case of prevention. The administration interval may be a specific time interval, and can be applied once a day, once every other day or once a week. In the case of prophylactic administration, administration may be carried out periodically at the rate of once every one to seven days, for example, and in the case of therapeutic administration, the isothiocyanic acid ester may be administered by single or multiple administrations. In general, in the case of treatment, one or two administrations given on the same day or on consecutive days promote scab formation.

The preventive and/or therapeutic agent for hairy wart disease of the present invention may be used in the form of a powder or formulated solid or liquid obtained by dissolving or dispersing in a solvent or dispersion medium such as water, may be sprayed in the form of a spray, or may be used in the form of a foam.

As was previously described, although the isothiocyanic acid ester can be used as the preventive and/or therapeutic agent for hairy wart disease of the present invention in the form of a water-soluble preparation, sprayable preparation or powdered composition, the preventive and/or therapeutic agent for hairy water disease of the present invention may also contain other components such as a wetting agent, antimicrobial agent, thickener, surfactant, colorant or fragrance in addition to the isothiocyanic acid ester used for the active ingredient.

Examples of wetting agents that can be used include moisturizing agents having the effect of moisturizing the skin, examples of which include glycerin, propylene glycol, sorbitol, lanolin, polyethylene glycol, lanolin-polyethylene glycol, lanolin-polyethylene glycol derivatives, aloe vera, allantoin and mixtures thereof.

Examples of antimicrobials that can be used include extracts and essential oils of plants having antimicrobial activity, specific examples of which include thyme, lemongrass, citrus fruits, lemons, oranges, anise, clove, aniseed, pine, cinnamon, geraniums, roses, mint, lavender, citronella, eucalyptus, peppermint, camphor, currum seed, sandalwood, rosemary, vervain, free grass, lemongrass, ratanya, Himalayan cedar and mixtures thereof.

Examples of thickeners that can be used include polymeric substances present in nature and their processed products (such as locust bean gum, gua gum, sodium alginate, sodium casein, ovalbumin, gelatin agar, carrageenan gum, sodium alginate, xanthan gum, quince seed extract, tragacanth gum, starch or processed starch), semi-synthetic polymeric substances (such as cellulose ethers (including hydroxyethyl cellulose, methyl cellulose, carboxymethyl cellulose and hydroxypropyl methyl cellulose), hydroxypropyl gua gum, soluble starch, cationic cellulose or cationic gua), and synthetic polymeric substances (such as carboxyvinyl polymers, polyvinylpyrrolidone, polyvinyl alcohol, polyacrylate polymers, polymethacrylate polymers, polyvinyl acetate polymers, polyvinyl chloride polymers or polyvinylidene chloride polymers).

Examples of surfactants that can be used include nonionic surfactants, anionic surfactants and cationic surfactants.

The preventive and/or therapeutic agent for hairy wart disease of the present invention normally contains an amount of an isothiocyanic acid ester that is effective against hairy wart disease, and preferably contains 5% by weight or more of an isothiocyanic acid ester.

Furthermore, although the prevention and/or treatment method of the present invention may use only an isothiocyanic acid ester as an active ingredient thereof, it may also be used in combination with other medicinal agents that are effective for the prevention and/or treatment of hairy wart disease, examples of which include sodium alginate, copper sulfate, slaked lime and antibiotics.

In addition, although the preventive and/or therapeutic agent of the present invention may contain only an isothiocyanic acid ester as an active ingredient thereof, it may also be used in combination with other medicinal agents that are effective for the prevention and/or treatment of hairy wart disease, examples of which include sodium alginate, copper sulfate, slaked lime and antibiotics.

EXAMPLES

Although the following provides a detailed explanation of the present invention through examples thereof, the present invention should not be interpreted as being limited to the following descriptions.

Example 1

Effect of Isothiocyanic Acid Ester on Digital Dermatitis 3 g of a powdered composition of allyl isothiocyanate (trade name: "Wasaouro Powder", Mitsubishi-Kagaku Foods Corp.) were placed on a piece of absorbent cotton and pressed against the affected area of dairy cows afflicted with digital dermatitis followed by wrapping with an elastic bandage to administer the allyl isothiocyanate to the affected area in the form of a patch and assessing the effect two days later. In addition, the effect of respectively administering sodium alginate and slaked lime using the same method was also assessed two days later. The results are shown in Table 1.

TABLE 1

| Type of medicinal agent | Degree of effect | | | |
| --- | --- | --- | --- | --- |
| | Very effective | Effective | Slightly effective | Ineffective |
| Sodium alginate | 0 | 1 | 2 | 2 |
| Slaked lime | 0 | 2 | 5 | 0 |
| Allyl isothiocyanate | 2 | 1 | 0 | 0 |

* Numbers indicate number of digits

Figure 2:
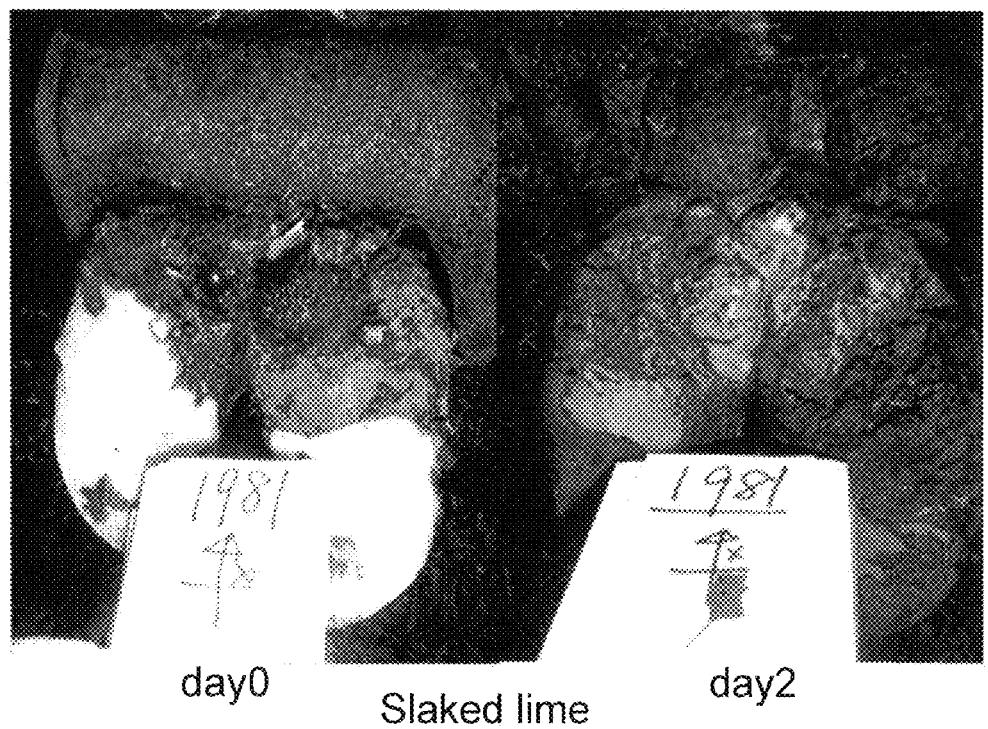
FIG. 2 is a photograph of an affected area at which the use of slaked lime was effective in Example 1.
Figure 3:
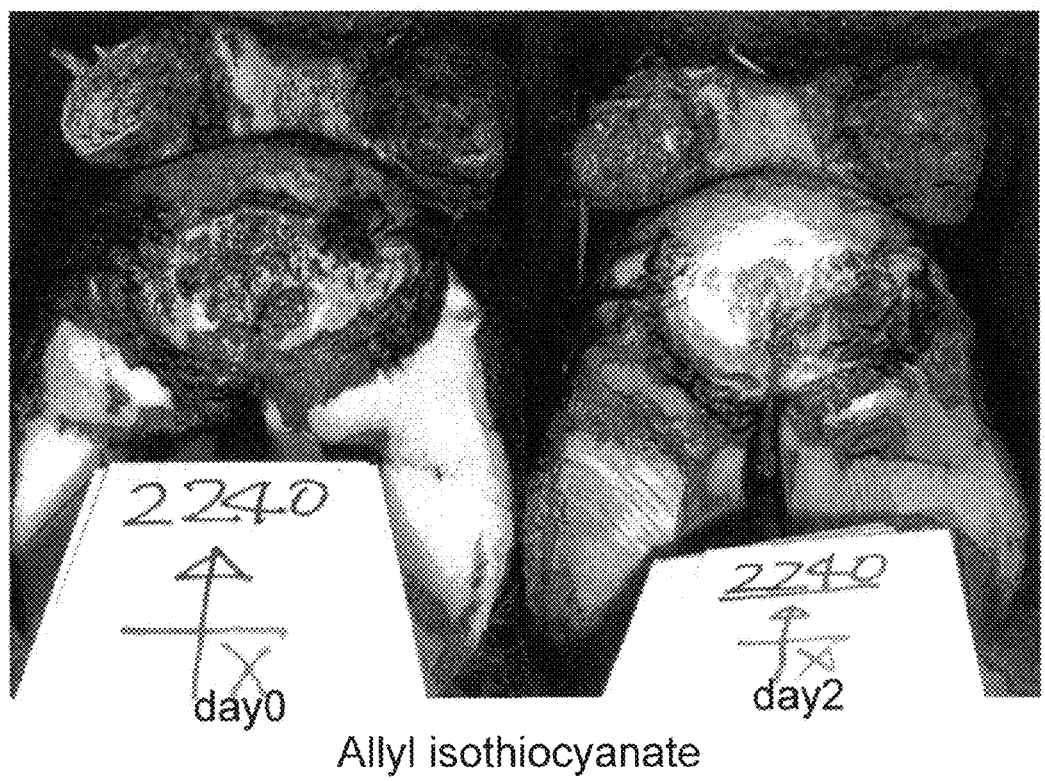
FIG. 3 is a photograph of an affected area at which the use of allyl isothiocyanate was very effective in Example 1.

As is clear from Table 1, in contrast to the percentage of digits for which the degree of the effect was effective or better being 20% in the case of sodium alginate and 29% in the case of slaked lime, that in the case of using allyl isothiocyanate was 100%. On the basis of the above results, allyl isothiocyanate was determined to have an extremely superior effect against digital dermatitis. A photograph of an affected area for which the use of sodium alginate was effective is shown in FIG. 1, a photograph of an affected area for which the use of slaked lime was effective is shown in FIG. 2, and a photograph of an affected area for which the use of allyl isothiocyanate was very effective is shown in FIG. 3. In comparison with the case of using sodium alginate or slaked lime, the degree of the effect in the case of using an isothiocyanic acid ester can be understood to clearly be higher.

Example 2

Figure 4:
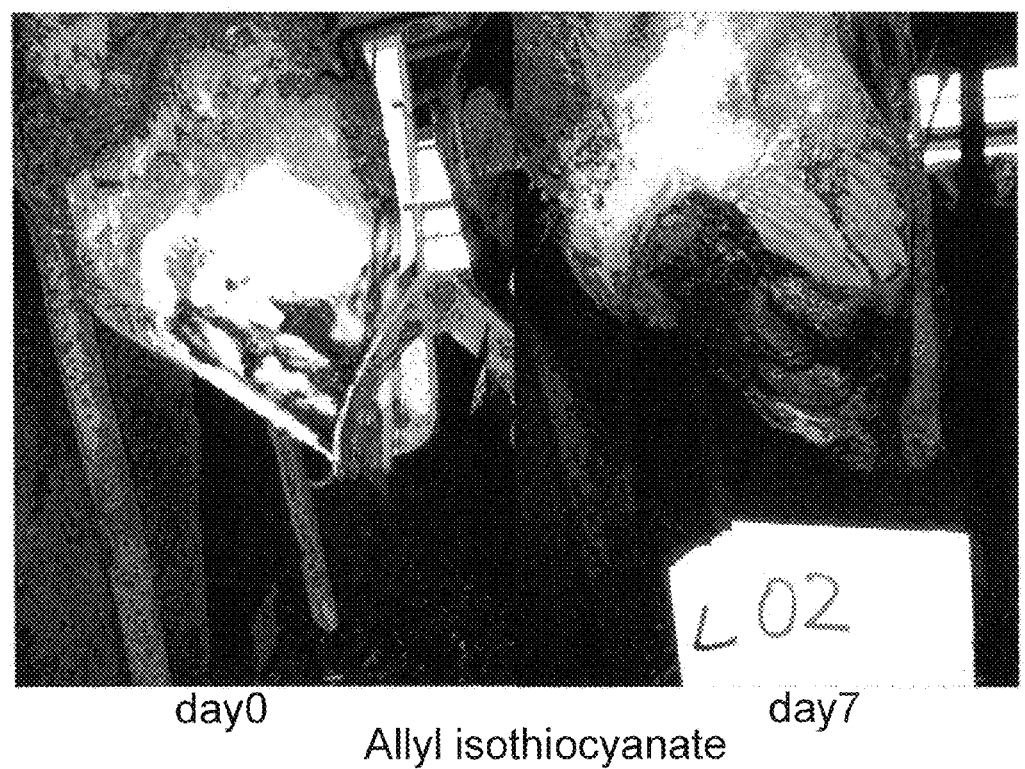
FIG. 4 is a photograph of an affected area that healed as a result of using allyl isothiocyanate in Example 2.

Effect of Isothiocyanic Acid Ester on Hairy Hoof Wart Attack 3 g of a powdered composition of allyl isothiocyanate (trade name: "Wasaouro Powder", Mitsubishi-Kagaku Foods Corp.) were placed on a piece of absorbent cotton and pressed against the affected area of dairy cows (5) afflicted with hairy hoof wart attack followed by wrapping with an elastic bandage to administer the allyl isothiocyanate to the affected area in the form of a patch and assessing the effect one week later. As a result, among the five dairy cows, the affected area healed in two of the cows, the affected area demonstrated improvement in one of the cows and the affected area was unchanged in one of the cows, with allyl isothiocyanate resulting in effects categorized as improved or better in the affected areas of four of the five dairy cows (a photograph of an affected area that healed is shown in FIG. 4). Hairy hoof wart attack is a hoof and leg disease having lesions that are more serious and cover a broader area in comparison with digital dermatitis, and when considering that an effective preventive and/or treatment method has currently yet to be found, this effect of allyl isothiocyanate can be said to be groundbreaking.

Example 3

Therapeutic Efficacy Test of Isothiocyanic Acid Ester Against Bovine Digital Dermatitis Samples were collected from two cows afflicted with digital dermatitis. First, a digital dermatitis lesion was collected from the affected area by biopsy prior to treatment. After collecting the lesion, a powdered composition containing allyl isothiocyanate (trade name: "Wasaouro Powder", Mitsubishi-Kagaku Foods Corp.) was applied to the affected area. After confirming improvement of clinical symptoms seven days later, a sample was again collected by biopsy. The stage of digital dermatitis at the time of sampling was assessed macroscopically. In order to investigate the predominant microbial species in the lesion before and after treatment, DNA was extracted from four specimens of digital dermatitis lesion materials of the two cows before and after treatment, low cycle number PCR (25 cycles or less) was carried out using universal primers to 16S rRNA gene, and the amplified gene fragment was cloned in an *Escherichia coli* vector. 192 clones were randomly harvested for each specimen to determine the base sequence of the amplified 16S rRNA gene. Among these, a homology analysis was performed by a BLAST search using clones from which data was obtained for base sequences in excess of 1450 bp, followed by determination of microbial species. The results for each cow are shown in Tables 2 and 3, respectively.

TABLE 2

| Microbial species | Before treatment (n = 181) | After treatment (n = 171) |
|---|---|---|
| Treponema | 79.6% | 7.0% |
| Eubacteriaceae | 5.5% | 0.6% | n indicates the number of clones for which data was obtained for base sequences in excess of 1450 bp. Percentages in the table indicate the percentages of clones for which microbial species were detected.

TABLE 3

| Microbial species | Before treatment (n = 180) | After treatment (n = 178) |
|---|---|---|
| Treponema | 37.8% | 0% |
| Clostridiaceae | 26.7% | 5.6% |
| Eubacteriaceae | 10.6% | 0.6% |
| Anaerovorax odorimutans | 10.0% | 0% |
| Acholeplasma vituli | 3.9% | 0% |
| Psychrobacter | 2.2% | 0% | n indicates the number of clones for which data was obtained for base sequences in excess of 1450 bp. Percentages in the table indicate the percentages of clones for which microbial species were detected.

The stage of digital dermatitis in both cows was M4 at the time of sample collection before treatment and M2 at the time of sample collection after treatment, thereby confirming a therapeutic effect. As is clear from Tables 2 and 3, although Treponema species were detected at a high frequency from all samples before treatment, Treponema species were detected at an extremely low frequency from the samples after treatment.

On the basis thereof, Treponema species were suggested to be present as the predominant microbial species in digital dermatitis lesions prior to treatment and are therefore considered to be a promising candidate for the cause of digital dermatitis. Since improvement of clinical symptoms was observed and the detection rates of Treponema species from samples after treatment were extremely low following application of isothiocyanic acid ester to the lesion, isothiocyanic acid ester is recognized to demonstrate a high level of antimicrobial activity against Treponema species while also being useful as a therapeutic agent for digital dermatitis.

Example 4

Effect of Isothiocyanic Acid Ester on Digital Dermatitis (with and without Hoof Trimming)

Allyl isothiocyanate (trade name: "Wasaouro Powder", Mitsubishi-Kagaku Foods Corp.) was applied to the affected areas of dairy cows afflicted with digital dermatitis, and microbial scores and changes in pain at the lesions were observed after 2, 4 and 6 days.

Comparisons were made under the following conditions A to D in order to confirm differences in effects attributable to the presence or absence of hoof trimming.

A: Allyl isothiocyanate applied to affected area after hoof trimming

B: Allyl isothiocyanate applied to affected area without performing hoof trimming C: Allyl isothiocyanate applied after hoof trimming and cleaning the affected area with Oxydol disinfectant D: Affected area cleaned with Oxydol disinfectant after hoof trimming (without applying allyl isothiocyanate)

Microbial scores of the affected areas were obtained by scoring the number of microorganisms from a stamped specimen of the heel bulb in the manner indicated below.

3: Treponema covered the entire field of view

2: Large number of Treponema confirmed in the field of view

1: Treponema only occasionally confirmed

0: Treponema unable to be confirmed

Changes in pain were evaluated based on the level of pressure at which pain was felt by tightly squeezing the affected area with a pressure gauge. Larger values indicate lower levels of pain.

Figure 5:
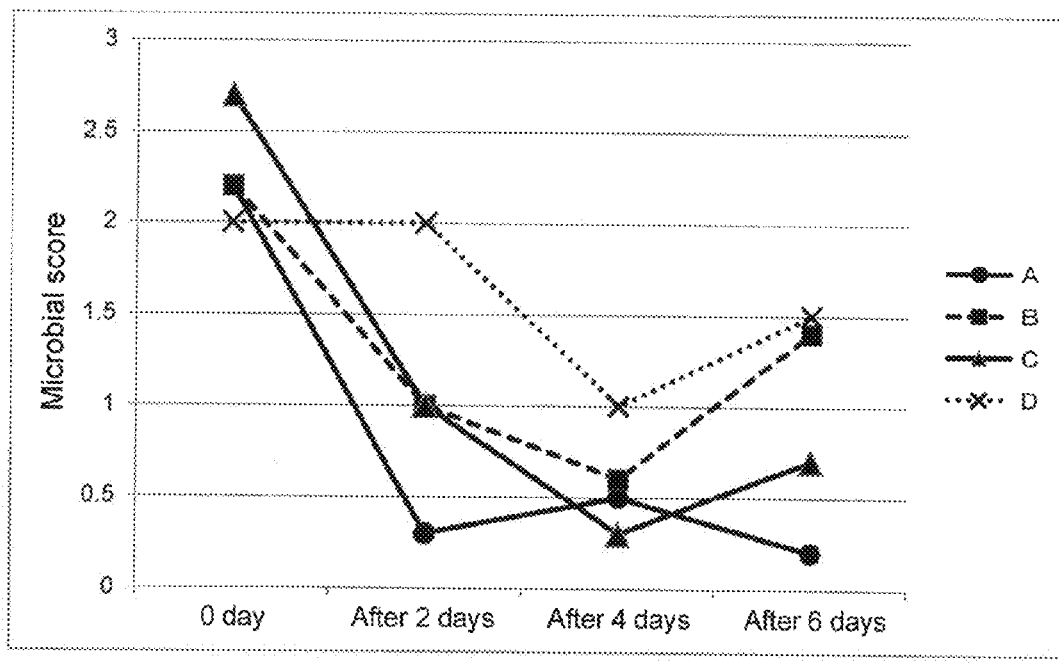
FIG. 5 is a graph showing differences in the effects of allyl isothiocyanate on microbial score at an affected area in Example 4 depending on the presence or absence of hoof trimming.
Figure 6:
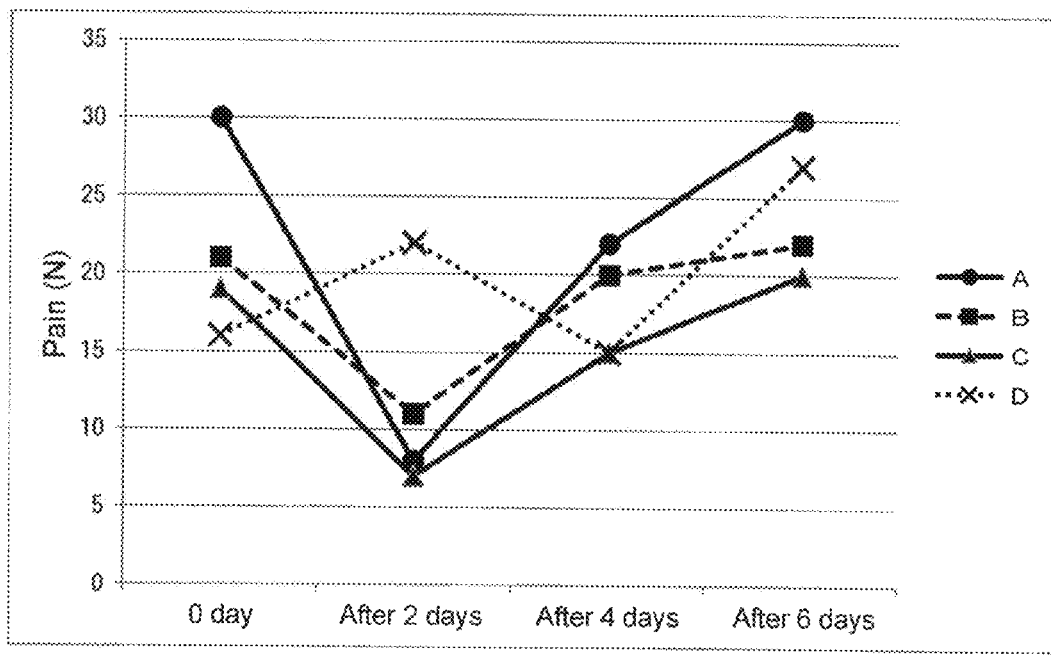
FIG. 6 is a graph showing differences in the effects of allyl isothiocyanate on pain at the affected area in Example 4 depending on the presence or absence of hoof trimming.

The results are shown in FIGS. 5 and 6.

The number of microorganisms at the lesion was determined to decrease when allyl isothiocyanate was administered after hoof trimming. In addition, the number of microorganisms at the lesion was determined to decrease further when allyl isothiocyanate was applied after cleaning the affected area with Oxydol disinfectant.

In addition, pain was determined to decrease when allyl isothiocyanate was applied after hoof trimming.

Example 5

Effect of Isothiocyanic Acid Ester on Digital Dermatitis (Administration Method)

A study was made of the method used to administer isothiocyanic acid ester to the affected areas of dairy cows afflicted with digital dermatitis. Administration was carried out by combining the following methods A1 to D1 as described in Tables 4 and 5 on day 0 and day 7, and lesion scores, obtained by scoring lesions (Table 4), and pain (Table 5) were evaluated on day 0, day 2, day 7, day 14 and day 21.

A1: Allyl isothiocyanate (Wasaouro Powder, Mitsubishi-Kagaku Foods Corp.) was mixed into 10 g of vaseline and applied to the affected area followed by wrapping with a bandage.

B1: Pine tar ointment was applied to the puncture site.

C1: 6 g and 3 g of allyl isothiocyanate (Wasaouro Powder, Mitsubishi-Kagaku Foods Corp.) were respectively placed in a bag (tea bag) composed of non-woven fabric. The bag containing 6 g was applied to the affected area while the bag containing 3 g was placed between the two portions of the hoof followed by loosely wrapping with a bandage, covering with a plastic bag and covering the plastic bag with a sock.

D1: Allyl isothiocyanate (Wasaouro Powder, Mitsubishi-Kagaku Foods Corp.) was mixed into 10 g of vaseline and applied to the affected area immediately after hoof trimming followed by covering the entire hoof with a plastic bag and covering the plastic bag with a sock.

Furthermore, lesion scores were as indicated below.

4: Dopfer classification M2; large ulcerative lesion

3: Dopfer classification M1; small ulcerative lesion

2: Dopfer classification M3; scab formation

1: Dopfer classification M4; Small

0: Dopfer classification M0; Normal

In addition, changes in pain were evaluated based on the level of pressure at which pain was felt by tightly squeezing the affected area with a pressure gauge. Larger values indicate lower levels of pain.

According to the results for lesion scores, the lesions were able to be cured in nearly all cases regardless of the administration method. In addition, pain was determined to tend to be able to be reduced in the case of using method C1.

TABLE 4

| Administration method | | Lesion scores | | | | |
|---|---|---|---|---|---|---|
| Day 0 | Day 7 | Day 0 | Day 2 | Day 7 | Day 14 | Day 21 |
| A1 | None | 3 | 2 | 2 | 1 | 1 |
| A1 | B1 | 3 | ND | 1 | 1 | ND |
| C1 | C1 | 3 | 1 | 2 | 0 | 0 |
| D1 | B1 | 2 | 2 | 2 | 1 | 1 |
| C1 | None | 2 | ND | 2 | 0 | 0 |
| C1 | B1 | 3 | 2 | 2 | 2 | 0 |

TABLE 5

| Administration method | | Pain | | | | |
|---|---|---|---|---|---|---|
| Day 0 | Day 7 | Day 0 | Day 2 | Day 7 | Day 14 | Day 21 |
| A1 | None | 0.47 | 5.7 | 33.8 | 4.7 | 37 |
| A1 | B1 | ND | ND | 13 | 35 | ND |
| C1 | C1 | 50 | 20 | 50 | 44 | 50 |
| D1 | B1 | 16.6 | 15.7 | 5.5 | 33 | 33 |
| C1 | B1 | 15.3 | 50 | 3.75 | 50 | 50 |

INDUSTRIAL APPLICABILITY

The present invention has the potential for industrial applicability in that it is able to provide a novel method for preventing and/or treating hairy wart disease which is a hoof and leg disease of ungulates.

The invention claimed is:

1. A method for treating hairy wart disease by administering a therapeutic composition comprising at least 5% by weight of an isothiocyanic acid ester as an active ingredient to a hoof of an ungulate in need thereof, wherein the isothiocyanic acid ester is a $C_{2-6}$ alkenyl isothiocyanate, aryl isothiocyanate, $C_{1-6}$ alkyl isothiocyanate, phenyl $C_{1-6}$ alkyl isothiocyanate or $C_{3-6}$ cycloalkyl isothiocyanate.

2. The method according to claim 1, wherein the isothiocyanic acid ester is a $C_{2-6}$ alkenyl isothiocyanate.

3. The method according to claim 1, wherein the isothiocyanic acid ester is administered to a hoof of an ungulate after hoof trimming.

4. A therapeutic agent for hairy wart disease, comprising at least 5% by weight of an isothiocyanic acid ester as an active ingredient thereof, wherein the isothiocyanic acid ester is a $C_{2-6}$ alkenyl isothiocyanate, aryl isothiocyanate, $C_{1-6}$ alkyl isothiocyanate, phenyl $C_{1-6}$ alkyl isothiocyanate or $C_{3-6}$ cycloalkyl isothiocyanate.

5. The therapeutic agent according to claim 4, wherein the isothiocyanic acid ester is a $C_{2-6}$ alkenyl isothiocyanate.

6. The method according to claim 1, wherein the therapeutic agent is sprayed, applied or affixed to an affected area of the hoof.

7. The method according to claim 1, wherein the therapeutic agent is a powdered composition.

8. The method according to claim 1, wherein the hairy wart disease is digital dermatitis.

9. The method according to claim 1, wherein the hairy wart disease is caused by a pathogen of the genus *Treponema*.

10. The therapeutic agent according to claim 4, which is in the form of a powdered composition.

11. A method for treating hairy wart disease by administering a therapeutic agent comprising at least 5% by weight of an isothiocyanic acid ester as an active ingredient thereof to a hoof of an ungulate in need thereof,
wherein the isothiocyanic acid ester is a $C_{2-6}$ alkenyl isothiocyanate, aryl isothiocyanate, $C_{1-6}$ alkyl isothiocyanate, phenyl $C_{1-6}$ alkyl isothiocyanate or $C_{3-6}$ cycloalkyl isothiocyanate, and
the therapeutic agent is sprayed, applied or affixed directly to an affected area.

* * * * *

UNITED STATES PATENT AND TRADEMARK OFFICE
CERTIFICATE OF CORRECTION

Page 1 of 1

PATENT NO. : 9,603,827 B2
APPLICATION NO. : 14/984655
DATED : March 28, 2017
INVENTOR(S) : Keiji Okada et al.

It is certified that error appears in the above-identified patent and that said Letters Patent is hereby corrected as shown below:

On the Title Page

Item (30), the Foreign Application Priority Data Information has been omitted. Item (30) should read:
-- (30)  Foreign Application Priority Data
Jul. 3, 2013     (JP).................................2013-139496 --

Signed and Sealed this
Second Day of October, 2018

Andrei Iancu
*Director of the United States Patent and Trademark Office*